(12) United States Patent
Ogle et al.

(10) Patent No.: US 11,478,371 B2
(45) Date of Patent: Oct. 25, 2022

(54) METHODS AND SYSTEMS FOR TREATMENT OF ANEURYSMS

(71) Applicant: Exovitra LLC, Edina, MN (US)

(72) Inventors: Matthew F. Ogle, Edina, MN (US); Brandon Gregory Walsh, Kaysville, UT (US)

(73) Assignee: Exovitra LLC, Edina, MN (US)

( * ) Notice: Subject to any disclaimer, the term of this patent is extended or adjusted under 35 U.S.C. 154(b) by 0 days.

(21) Appl. No.: 16/853,205

(22) Filed: Apr. 20, 2020

(65) Prior Publication Data

US 2021/0322191 A1    Oct. 21, 2021

(51) Int. Cl.
| | | |
|---|---|---|
| *A61F 2/962* | (2013.01) | |
| *A61F 2/07* | (2013.01) | |
| *A61F 2/95* | (2013.01) | |
| *A61B 17/12* | (2006.01) | |
| *A61F 2/90* | (2013.01) | |

(52) U.S. Cl.
CPC ........ *A61F 2/962* (2013.01); *A61B 17/12168* (2013.01); *A61F 2/90* (2013.01); *A61B 17/12118* (2013.01); *A61B 2017/1205* (2013.01); *A61F 2/07* (2013.01); *A61F 2/95* (2013.01)

(58) Field of Classification Search
CPC .... A61F 2/962; A61F 2/90; A61F 2/07; A61F 2/95; A61B 17/12168; A61B 2017/1205; A61B 17/12118
See application file for complete search history.

(56) References Cited

U.S. PATENT DOCUMENTS

| | | | |
|---|---|---|---|
| 5,405,379 A * | 4/1995 | Lane | A61F 2/95 623/1.2 |
| 5,681,345 A | 10/1997 | Euteneuer | |
| 7,226,474 B2 | 6/2007 | Iancea et al. | |
| 8,845,716 B2 | 9/2014 | Lee et al. | |
| 2001/0041928 A1 * | 11/2001 | Pavcnik | A61F 2/07 623/1.13 |
| 2002/0029076 A1 * | 3/2002 | Yee | A61F 2/95 623/1.11 |
| 2002/0143385 A1 * | 10/2002 | Yang | A61F 2/07 623/1.13 |
| 2003/0074049 A1 * | 4/2003 | Hoganson | A61F 2/07 623/1.13 |

(Continued)

FOREIGN PATENT DOCUMENTS

WO    WO-2021216268 A1    10/2021

OTHER PUBLICATIONS

"International Application Serial No. PCT/US2021/025561, International Search Report dated Jul. 16, 2021", 2 pgs.

(Continued)

*Primary Examiner* — Jing Rui Ou
(74) *Attorney, Agent, or Firm* — Schwegman Lundberg & Woessner, P.A.

(57) ABSTRACT

A method and device include attaching a tether portion of a sleeve to a distal end of a catheter, placing the distal end of the catheter into a selected position within a vessel, moving a stent through a lumen of the catheter, retentively engaging a first end of the stent with a distal end of the sleeve, and detaching the sleeve about the tether portion such that the sleeve covers at least a portion of the stent at the selected position within the vessel.

17 Claims, 9 Drawing Sheets

(56) References Cited

U.S. PATENT DOCUMENTS

| | | | |
|---|---|---|---|
| 2004/0106978 A1* | 6/2004 | Greenberg | A61F 2/95 623/1.13 |
| 2004/0148010 A1* | 7/2004 | Rush | A61L 31/10 606/154 |
| 2005/0121043 A1 | 6/2005 | Abrams | |
| 2006/0129215 A1* | 6/2006 | Helmus | A61L 27/56 607/115 |
| 2006/0259131 A1* | 11/2006 | Molaei | A61F 2/07 623/1.44 |
| 2007/0162106 A1* | 7/2007 | Evans | A61B 17/12136 623/1.23 |
| 2008/0004653 A1* | 1/2008 | Sherman | A61B 17/12022 606/195 |
| 2009/0069880 A1* | 3/2009 | Vonderwalde | A61B 17/12022 623/1.13 |
| 2011/0015718 A1 | 1/2011 | Schreck | |
| 2012/0296406 A1* | 11/2012 | Minion | A61F 2/07 623/1.11 |
| 2017/0079817 A1* | 3/2017 | Sepetka | A61F 2/88 |

OTHER PUBLICATIONS

"International Application Serial No. PCT/US2021/025561, Written Opinion dated Jul. 16, 2021", 5 pgs.

* cited by examiner

METHODS AND SYSTEMS FOR TREATMENT OF ANEURYSMS

BACKGROUND

Subarachnoid Hemorrhage (SAH) is the most fatal type of stroke with mortality rates between 30-60% and only ⅓ of survivors returning to an independent life. SAH occurs when there is bleeding from a ruptured intracranial aneurysm, which is a dilation or ballooning of a blood vessel of the brain. Current treatment of unruptured intracranial aneurysms (UIA) consists of blocking the aneurysm. This is accomplished either surgically (by opening the head) or through an endovascular route (from within blood vessels). Regardless of approach treatment remains dangerous with high in-hospital complication rates and long-term recurrence rates for both procedures.

Flow diverting stents have been suggested for delivery during endovascular route, e.g., to provide a scaffold across wide necked aneurysms. Once introduced within a blood vessel across the neck of an aneurysm, the mesh of the stent may slow blood flow into the aneurysm. For example, the mesh may have a porosity intended to slow flow into the aneurysm yet maintain patency of side branches and/or perforating arteries extending from the blood vessel within which the stent is implanted. In some vascular disease states, it is not safe or advised to perfuse these ancillary arteries, e.g. Cavernous aneurysms where the excessive pressures will still cause dilatation or rupture. In these cases, it would be better to cover a portion or the whole stent.

Stent have been suggested for such applications, however, stents porosity needed can increase the profile of the stent, which may make delivery more difficult due to increased stiffness of the stent and/or a larger catheter being needed to deliver the stent.

It has also been suggested to deliver covered stents into a vessel across an aneurysm such that a desired porosity may be attained based on covering the stents. However, this requires delivering through very large catheters to accommodate increased modified stent size, which can extend and/or otherwise complicate the procedure.

SUMMARY

A method and device include attaching a tether portion of a sleeve to a distal end of a catheter, placing the distal end of the catheter into a selected position within a vessel, moving a stent through a lumen of the catheter, retentively engaging a first end of the stent with a distal end of the sleeve, and detaching the sleeve about the tether portion such that the sleeve covers at least a portion of the stent at the selected position within the vessel.

DETAILED DESCRIPTION

Figure 1:
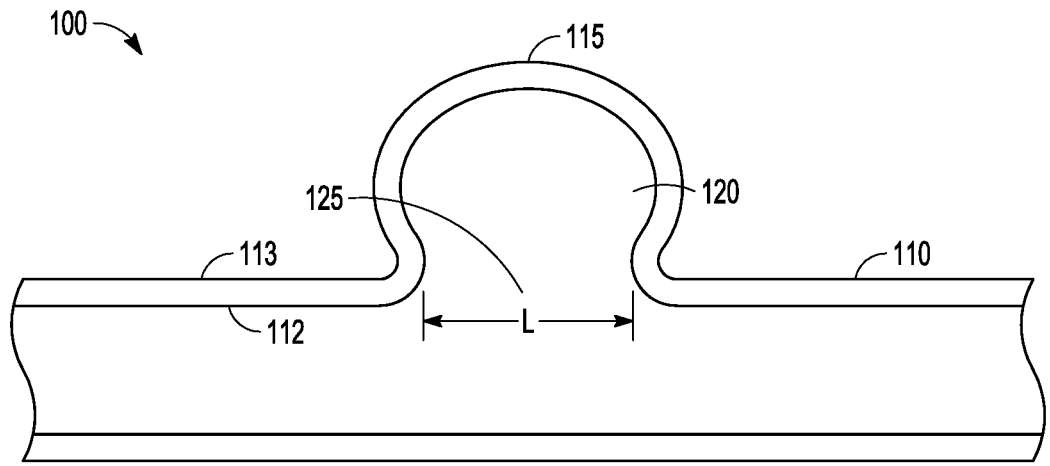
FIG. 1 is a cross section representation of a vessel with an aneurysm according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The present disclosure relates generally to medical methods and devices for the treatment of neurovascular aneurysms. An aneurysm is an excessive localized enlargement of an artery caused by a weakening of the artery wall. Methods and systems are described for covering the outer dimension of a stent with a sleeve to prevent blood communication by occluding vascular aneurysms of the cerebral arterial vasculature.

A stent is an implantable scaffold that is typically delivered percutaneously and deployed in a vein, artery, or other tubular body organ. A sent may be radially expanded in situ, thereby expanding and/or supporting the vessel wall or body organ wall. In particular, stents are quite commonly implanted in the coronary, cardiac, pulmonary, neurovascular, and peripheral vascular vessels. Conventional stent technology is relatively well developed. Conventional stent designs typically feature a straight tubular, single type cellular structure, configuration, or pattern that is repetitive through translation along a longitudinal axis.

Many stents may be coated with bio-active surface coatings such as drugs to provide localized delivery. Systemic delivery of drugs is inherently limited since it is difficult to achieve constant drug delivery to the afflicted region and since systemically administered drugs often cycle through concentration peaks and valleys, resulting in time periods of toxicity and ineffectiveness. Therefore, to be effective, many drugs should be delivered in a localized manner. One approach for localized drug delivery utilizes stents as delivery vehicles. Smaller stents, such as those for use in brain aneurysms may be difficult to effectively coat with an effective amount of a drugs or cells.

The use of a sleeve to cover a stent as described herein also enables better control and higher doses of drugs and/or cells to be added to the sleeve. In one embodiment, mesenchymal stem cells (MSCs) may be coated on the sleeve and thereby delivered to the site of an intracranial aneurysm. Such a sleeve coating may offer a less invasive means to stabilize or even repair an aneurysm prior to rupture. The use of a sleeve covered stent enables a catheter-based device to deliver cellular therapeutics to the site of aneurysms, associating the MSC to the outside of the sleeve as a delivery systems.

FIG. 1 is a cross section representation of a vessel 100, such as an arterial blood vessel. The vessel may be an intracranial vessel. The vessel 100 includes a wall 110 forming a generally tubular shape. Wall 110 includes an inside 112 and an outside 113. In some vessels, a portion of the wall 110 may be weaker than other portions. Pressure from a fluid in the vessel 100 may cause the weak portion to bulge as indicated at 115, forming an enlarged inner portion 120 of the vessel 100. The weak portion results in a discontinuity of the vessel as indicated at 125. The length of the discontinuity is shown as "L" in FIG. 1. The bulge 115 is generally referred to as an aneurysm, with the discontinuity referred to as a face of the aneurysm. Intercranial aneurysms can be very dangerous due to the chances of rupture from arterial blood pressure.

Figure 2:
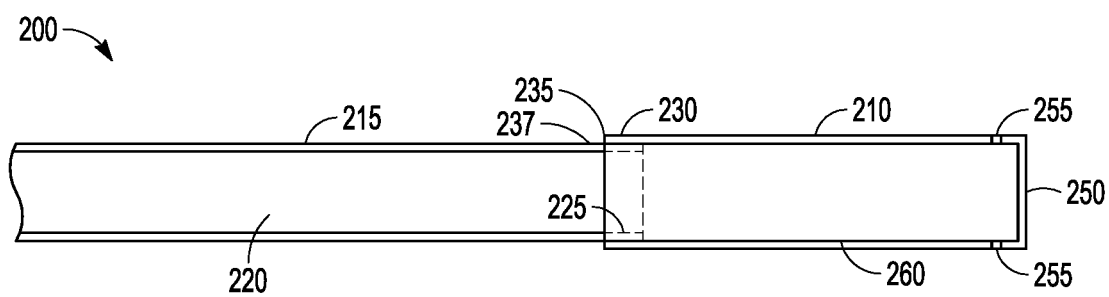
FIG. 2 is a cross section representation of a device that includes a sleeve tipped catheter according to an example embodiment.

FIG. 2 is a cross section representation of a device 200 that includes a sleeve 210 tipped catheter 215. The catheter 215 is a long tube having a hollow interior referred to as a lumen 220. The catheter 215 may be conventional and have a length generally between 130 to 150 cm. Only a distal portion of the catheter 215 is shown for convenience of illustration. A proximal end where equipment and devices may be inserted is not shown. A distal end or tip 225 of the catheter 215 has a sleeve proximal end 230 attached as indicated at attachment point 235. The sleeve 210 may be attached to the tip 225 at an outside wall 237 of the catheter 215 via adhesives, heat, or other means to retain the sleeve while the catheter tip is inserted into a vessel a desired distance.

The sleeve proximal end 230 may be referred to as a tethered portion 230. The tethered portion 230 may include perforations that release the sleeve at a desired time as described below. Other means of releasing or detaching the sleeve about the tethered portion 230 may include electrical current to melt, chemicals to dissolve, or heat to melt the tethered portion and release the sleeve. Sleeve 210 may include a distal end 250 that includes one or more holes 255. The portion of sleeve 210 between the distal end 250 and the tethered portion 230 may be referred to as a cover portion 260. In further embodiments, reference number 255 is representative of loops that may be formed on an inside of the sleeve 210.

In various embodiments, sleeve 210 may be cylindrical or a tapered cylindrical structure that is deformable. Sleeve 210 may be formed of one or more polymers for example, including a single polymer, layered polymers, or a blend of polymers for example. Example polymers include polytetrafluoroethylene and polyurethane. Other deformable materials may be used in further examples. Different length portions of the sleeve may have different properties. The tether portion may be thinner in one embodiment. In one embodiment, the sleeve has an axial length of between 1 mm and 100 mm and the length and a wall thickness of between 0.00635 mm and 0.127 mm.

Figure 3:
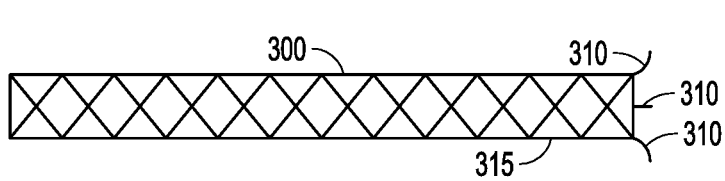
FIG. 3 is a cross section representation of a stent adapted to capture a sleeve according to an example embodiment.

FIG. 3 is a cross section representation of a stent 300 adapted to capture the sleeve 210 and end up coated by the sleeve 210. Stent 300 may be formed as a straight tubular, single type cellular structure, configuration, or pattern that is repetitive through translation along a longitudinal axis. Stent 300 may be expandable such as by use of a dilator such as an elongated balloon or other mechanism commonly used to expand stents. In one embodiment, stent 300 includes one or more struts 310 at a distal end 315. In one example, the catheter comprises a microcatheter and the stent has a diameter less than 0.0762 mm. These dimensions or smaller are useful for treating cerebral vessel aneurysms, where the vessels may be quite small. Larger dimensions may be used to treat other vessels with or without aneurysms, such as renal vessels or even pipes.

Figure 4:
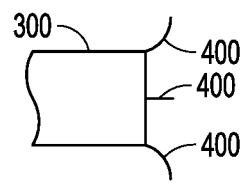
FIG. 4 is a block diagram representation of a portion of the distal end of a stent according to an example embodiment.

FIG. 4 is a block diagram representation of a portion of the distal end 315 of stent 300. Example struts 400 are shown as extending radially from the end of the stent and forming an arc back towards an axis of the stent. The strut thus forms a curved structure that operations to mate with the one or more holes 255 of the sleeve 210 as the stent 300 is moved relative to the sleeve. The curvature of the struts helps ensure that damage to a vessel is minimized, yet upon encountering a hole in the sleeve 210, the strut 400 captures the sleeve 210. In further embodiments, the struts 310 need not be curved, as the stent may be positioned within the plenum to its final installed position. Withdrawing the catheter causes the sleeve to move relative to the fixed position stent. Without movement of the struts 310 adjacent vessel walls, minimal to no damage to the vessel is likely to occur. The struts may also be used to engage with loops, also represented and referenced as 255.

Figure 5:
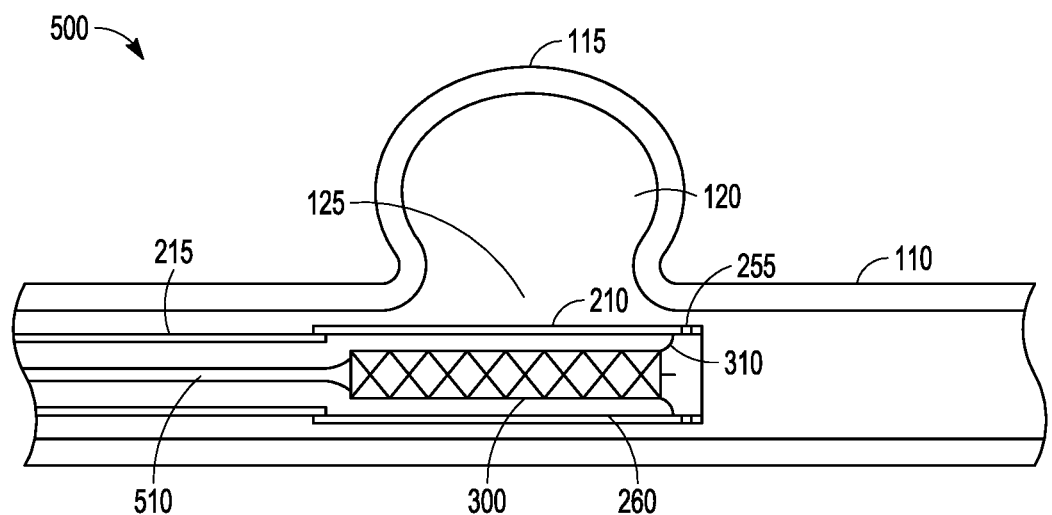
FIG. 5 is a block representation of installation of a stent and sleeve combination into the vessel with an aneurysm according to an example embodiment.

FIG. 5 is a block representation 500 of installation of a stent 300 and sleeve 210 combination into the vessel 110 with an aneurysm 115. Reference numbers for like components are consistent with reference numbers used in prior figures. The stent 300 has been moved through the lumen 220 of the catheter 215 to a position covering the discontinuity 125 of the vessel. The stent 300 may be moved via a rod 510 to the desired position. The position may be verified via the use of a fluoroscope or other commonly used mechanism. In some embodiments, one or more positional markers may be attached to the stent 300 to facilitate placement of the stent within the vessel in a known manner.

In one embodiment a deformable sleeve-tipped catheter 215 may be proximate the aneurysm 115 in the vessel 110. Being placed proximate the aneurysm comprises being placed in a position to accomplish a desired goal of treating the aneurysm. One such placement includes ensuring that the stent 300 is in a position to extend a desired amount on both sides of the aneurism such that withdrawal of the catheter 215 results in the stent completely blocking the length L of the aneurysm.

One or more struts 310 of the stent 300 are shown as having engaged the sleeve 210 via holes 255. In addition, either the stent has been pushed through sleeve, or the catheter has been withdrawn with the rod 510 holding the stent 300 in position so that the sleeve covers the stent as shown. The stent 300 as shown is in a crimped position.

Figure 6:
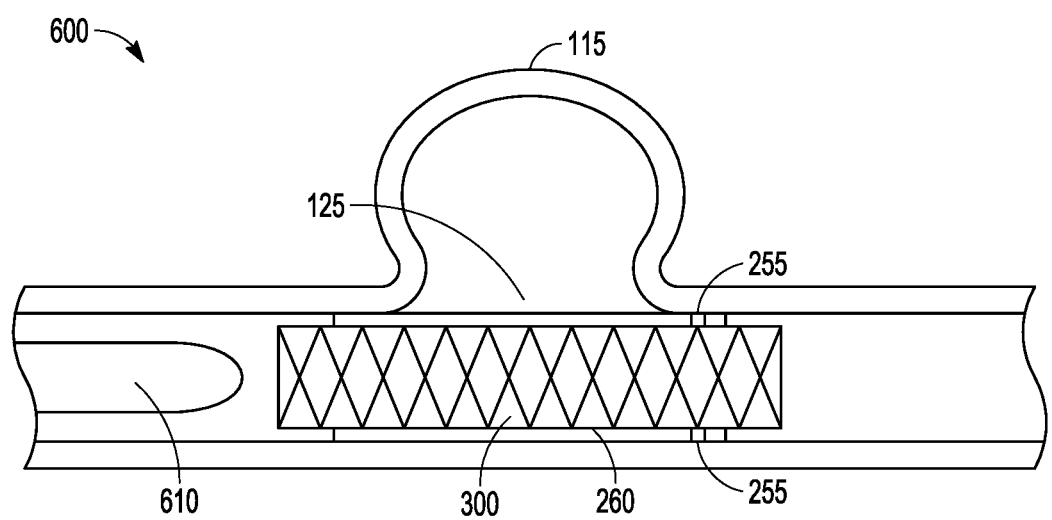
FIG. 6 is a block representation of an installed stent and sleeve cover portion serving to block a discontinuity according to an example embodiment.

FIG. 6 is a block representation 600 of the installed stent 300 and sleeve cover portion 260 serving to block the discontinuity 125. The stent 300 may be radially expanded to contact and press against the inner wall 112 of vessel 110 through the sleeve cover portion 260. The stent 300 may be expanded via conventional means, such as via an inflatable balloon 610 shown as being withdrawn.

The sleeve cover portion 260 may become dilated via the expansion of the stent 300 such that the sleeve becomes enmeshed in an outer surface of the stent. The sleeve cover portion 260 may also be coated with bio-active surface coatings referred to as therapeutics, such as drug or cellular therapeutics or both. An outside portion of the sleeve may be so covered. Different portions of the cover portion 260 may be coated or embedded with different therapeutics. Expansion of the stent and dilation of the sleeve causes cells in the vessel wall to slightly expand, which may increase acceptance of therapeutic coatings into the cells. The dilated sleeve may also increase the structural integrity of the stent, allowing a reduction in the size of the stent, and also enabling a reduction in the structure of the stent such that less metal may be used in forming the stent.

FIG. 6 also illustrates that the sleeve cover portion 260 is detached from the tether portion of the sleeve attached to the catheter. In FIG. 6, the struts 255 are located a desired distance on the stent away from the distal end of the stent. This results in the sleeve cover portion being set back a distance from the distal end of the stent. As shown, the cover does not extend all the way to the proximal end of the stent, such that only a middle portion of the stent is covered by the sleeve cover portion. By varying the length of the cover portion and the placement of the struts, a selected portion of the stent may be covered. In further embodiments, the cover may extend at least to one or both ends of the stent.

Figure 7:
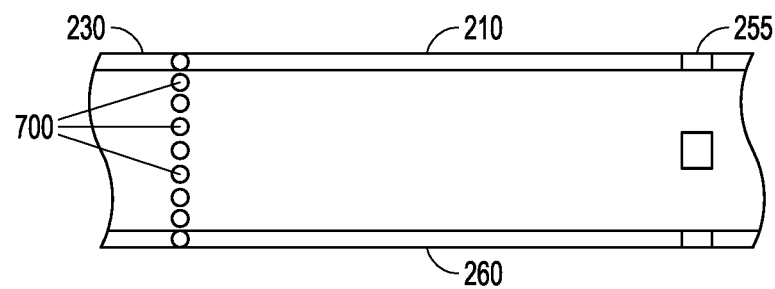
FIG. 7 is a block cross section of a sleeve illustrating a tether portion for attaching to the distal end of a stent according to an example embodiment.

FIG. 7 is a block cross section of sleeve 210 illustrating the tether portion 230 for attaching to the distal end of the stent. The tether portion 230 includes an annular ring of perforations 700. The plurality of perforations formed at a circumference of the sleeve are at a predetermined axial location of the sleeve. The perforations may be formed by use of a laser in one embodiment. The perforations form a weak link allowing separation of the tether portion from the cover portion just by pulling the tether portion away from the cover portion. The cover portion is held in place by the stent being engaged with the holes 255. Pulling back the catheter while holding the stent in place results in the separation. Once covered portion is separated, the stent is covered. Once radially expanded, the stent and cover are retained in place in the vessel.

Figure 8:
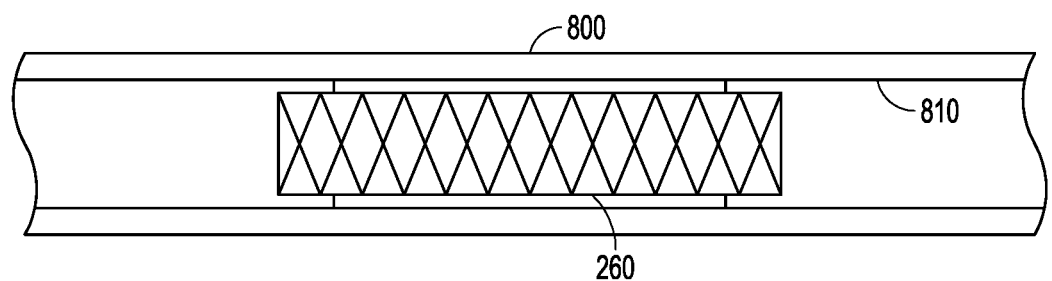
FIG. 8 is a block representation of an installed stent and sleeve cover portion in a vessel according to an example embodiment.

FIG. 8 is a block representation 800 of the installed stent 300 and sleeve cover portion 260 in a vessel 810. The stent may be used to enlarge a narrowed portion of the vessel with the sleeve including therapeutics for targeted delivery. Note that the inside of the sleeve may be coated with therapeutics. Both sides may be so coated in further embodiments with the same or different therapeutics. The stent may also be coated in further embodiments.

Figure 9:
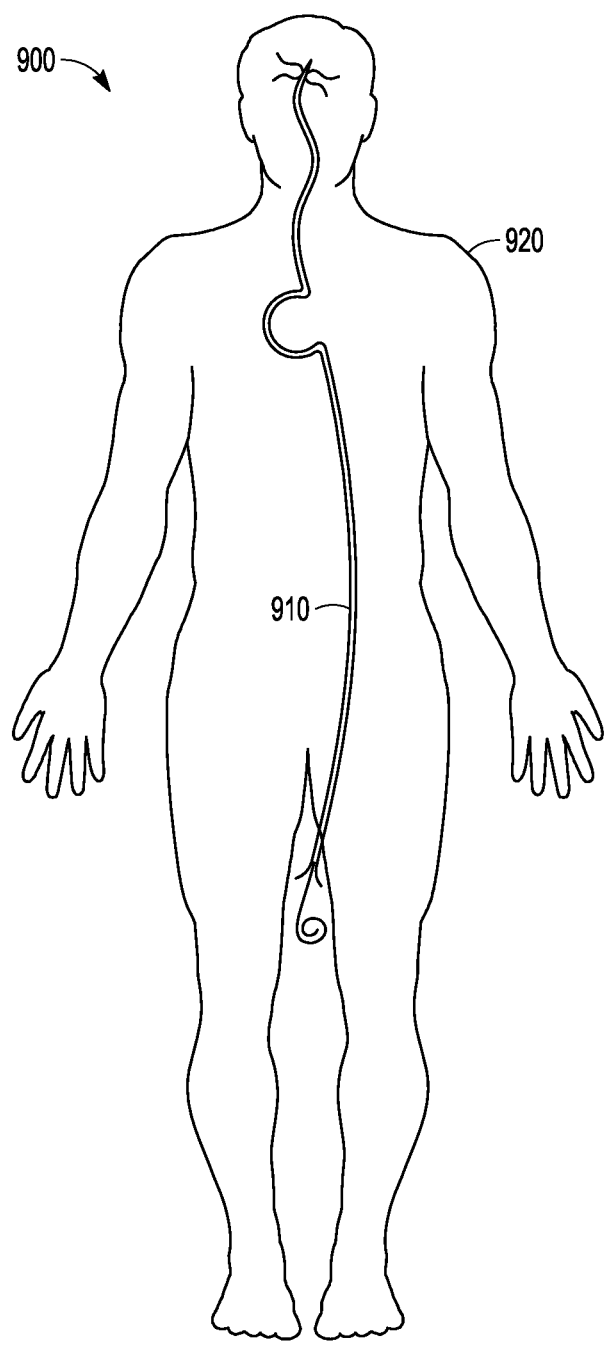
FIG. 9 is a block diagram illustrating use of a catheter to deliver and cover a stent with a sleeve according to an example embodiment.

FIG. 9 is a block diagram 900 illustrating use of a catheter to deliver and cover a stent with a sleeve according to example embodiments. A catheter 910 is shown as inserted into a human body 920. The catheter 910 may be inserted in an artery, such as femoral artery located about a groin area of the body 920. Once inserted a pusher 930 may be used to push the stent through the catheter to the desired location. The pusher may maintain force on the stent as the catheter is partially withdrawn to detach the cover portion from the tether portion, resulting in the stent being at least partially covered by the covering portion of the sleeve. The stent may then be expanded into place via the use of an elongated balloon threaded through the catheter and into contact with the insides of the stent. Expansion of the balloon expands the stent and dilates the cover portion of the sleeve. The balloon and catheter may then be withdrawn, leaving the stent in place.

Figure 10:
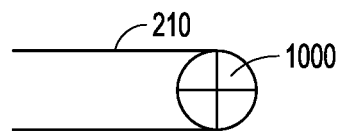
FIG. 10 is a perspective view of a distal end of sleeve for engaging with a stent according to an example embodiment.

FIG. 10 is a perspective view of a distal end of sleeve 210 illustrating an alternative means of engaging the sleeve with the stent according to an example embodiment. Instead of openings, the distal end of the sleeve 210 may include one or more strings 1000 that engage with the distal end of the stent to hold the sleeve during relative movement of the stent and the sleeve to cover the stent. The strings may form a cross hatch as shown or may be a web or other structure that can engage with the stent and hold the sleeve in place during installation. The strings may be formed of a material that will inertly decay within the vessel or may remain in place without interfering with blood flow through the vessel and stent.

Figure 11:
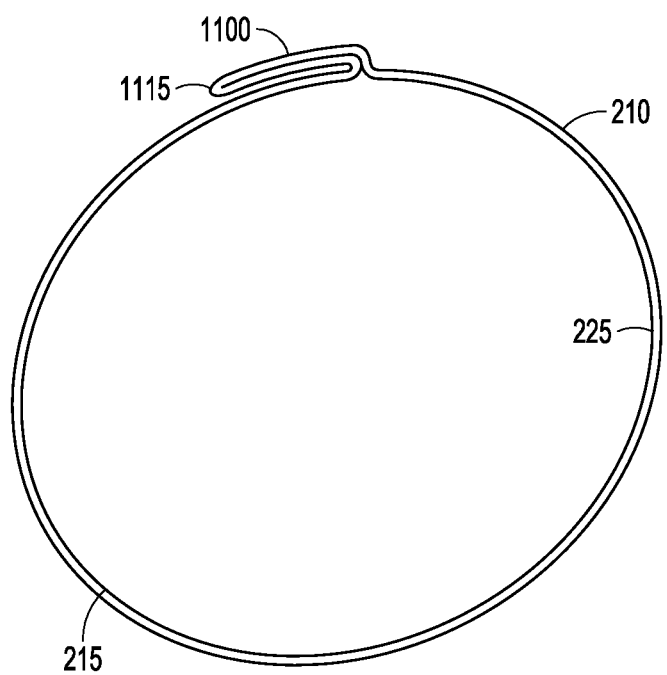
FIG. 11 is a radial cross section view of a representation of a distal end of a catheter with a folded sleeve according to an example embodiment.

FIG. 11 is a radial cross section view of a representation of the distal end 225 of the catheter 215. In this example, the sleeve 210 is shown attached to the catheter distal end 225 with a portion of the sleeve 210 folded over as indicated at 1110. The fold 1110 allows a larger diameter sleeve to be used. The fold 1110 allows for dilation of the sleeve in response to radial expansion of the stent without the sleeve having to stretch more than a desired amount as determined by the amount of overlap. An end of the overlapping portion of the sleeve may be lightly held in place via a heat seal indicated at 1115. The seal or other means of attachment, such as adhesive or mechanical means will be easily broken by the radial expansion of the stent, or by separation of the tether portion 230 of the sleeve from the cover portion.

Figure 12A:
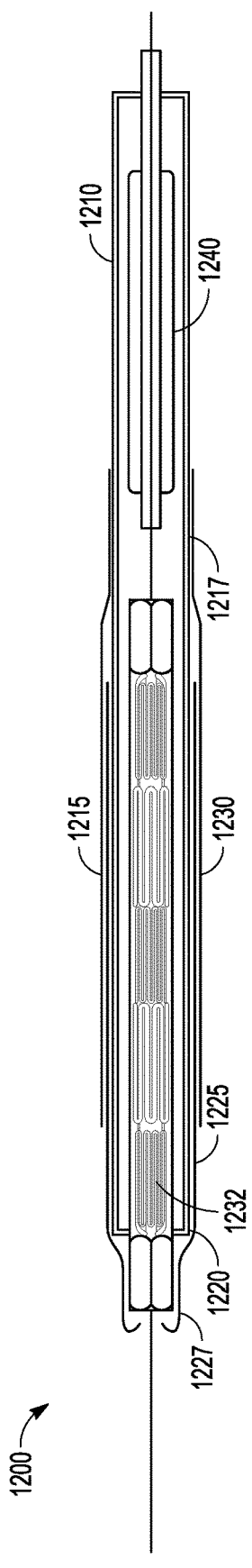
FIGS. 12A and 12B are side cross section representations of an alternative device for placing a sleeve coated stent in a desired position in a vessel according to an example embodiment.
Figure 12B:
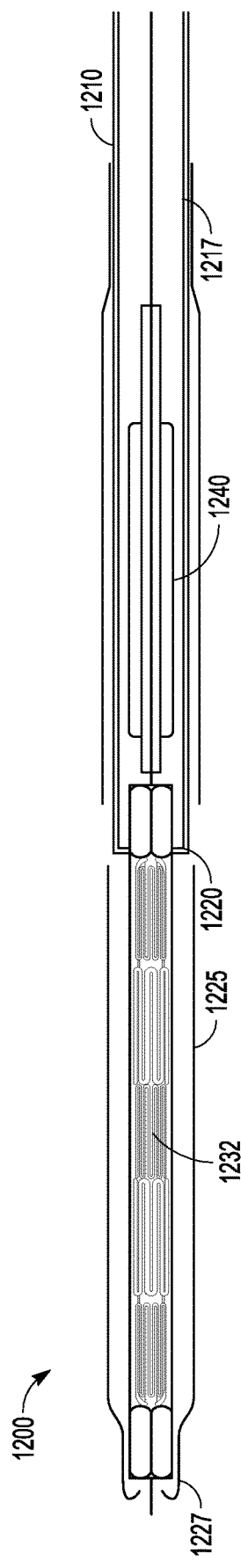

FIGS. 12A and 12B are side cross section representations of a device 1200 that includes a microcatheter 1210 having an outer sheath 1215 retentatively coupled to the microcatheter 1210 at a selected position 1217 from a distal end 1220 of the microcatheter 1210. The outer sheath 1215 expands slightly from the position 1217 towards the distal end 1220 of the microcatheter to provide space for a graft or sleeve 1225 between the outer sheath 1215 and the microcatheter 1210. The sleeve 1225 may be held in place by the outer sheath 1215 during installation.

The outer sheath 1215 extends from the position 1217 almost to the distal end 1220 of the microcatheter 1210 in one embodiment as illustrated at 1230. The outer sheath 1215 serves to protect the sheath 1225 during insertion of the device 1200 into a vessel to a desired position at end 1220, decreasing the possibility of friction resulting from such insertion undesirably moving the sheath 1225. The end of outer sheath 1215 may vary in position to be spaced back from the end 1220 of the microcatheter to being even or even extending slightly past the end 1220 of the microcatheter 1210 in different embodiments.

The sleeve 1225 narrows in diameter at 1227 past the distal end 1220 of the microcatheter 1210 to facilitate retentive engagement with a stent 1232 during installation of the stent 1232 at a desired position within the vessel. Typical lengths of the sheath 1215 may range from 1 mm to 150 mm or longer. As illustrated in FIGS. 12A and 12B, the stent 1232 is in contact with the narrowed end of the sleeve 1225 and is slightly extending from the end of the microcatheter 1210. A rod 1240 may be used to hold the stent in position as the microcatheter 1210 is being withdrawn. Rod 1240 is also representative of a balloon that can push and hold the stent 1230 and then engage on the interior diameter for further dilation. At the same time, the sleeve 1225 is also pulled off, or dragged along the microcatheter to cover the stent 1232 as illustrated in FIG. 12B. Note that in FIG. 12B, the stent 1232 has not yet been expanded.

Figure 13:
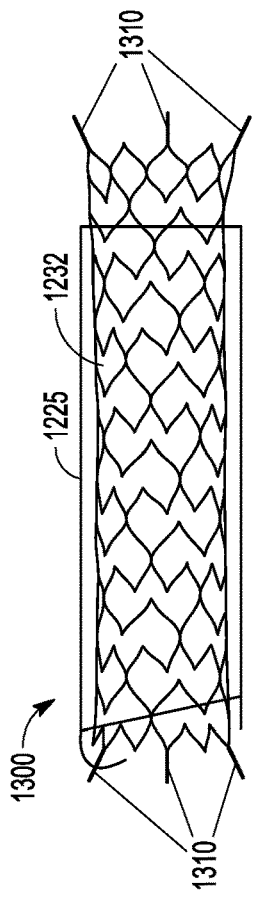
FIG. 13 is a side elevation view of an example expanded stent according to an example embodiment.

FIG. 13 is a side elevation view of an example expanded stent 1300. The stent 1300 may be constructed as a looped mesh and has multiple struts 1310 that may be formed from mesh loops. The struts 1310 help engage the narrowed end of the sleeve 1225 as the microcatheter 1210 is withdrawn. One or both ends of the stent 1300 may include such struts 1310.

Figure 14:
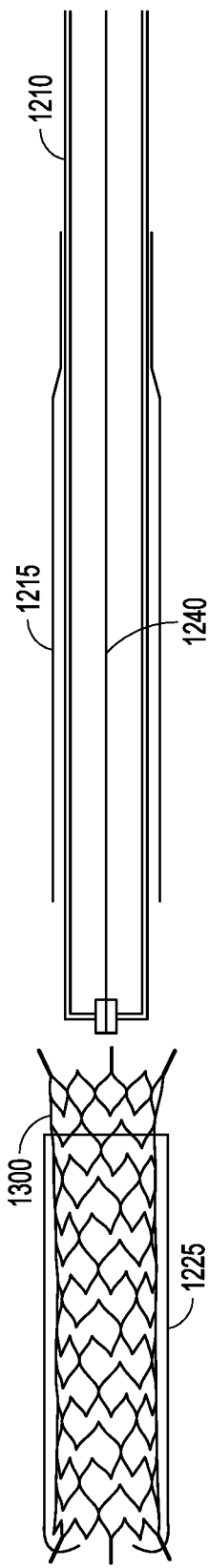
FIG. 14 is a side view illustrating a stent covered by a sleeve according to an example embodiment.

FIG. 14 is a side view illustrating stent 1300 covered by the sleeve 1225 following withdrawal of the microcatheter 1210. The sleeve 1225 in this example embodiment is shown extending along a substantial length of the stent 1300.

Figure 15:
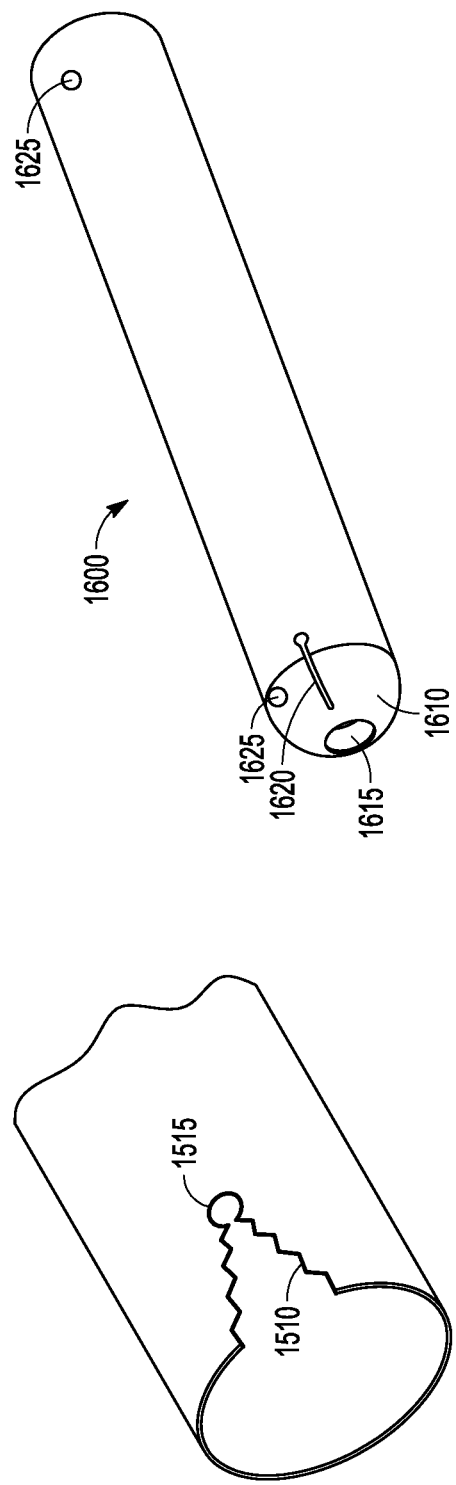
FIG. 15 illustrates an end of a sleeve that has a feature that has been torn according to an example embodiment.

FIG. 15 illustrates an end of the sleeve 1225 that has a feature 1510 that has been torn such as by expansion of a balloon such that the narrowed end of the sleeve does not interfere with flow within the vessel in which it has been installed. The feature 1510 may comprise a slot that ends in a hole 1515 with a larger diameter than the width of the slot to prevent further tearing of the sleeve 1225 past the hole.

Figure 16:
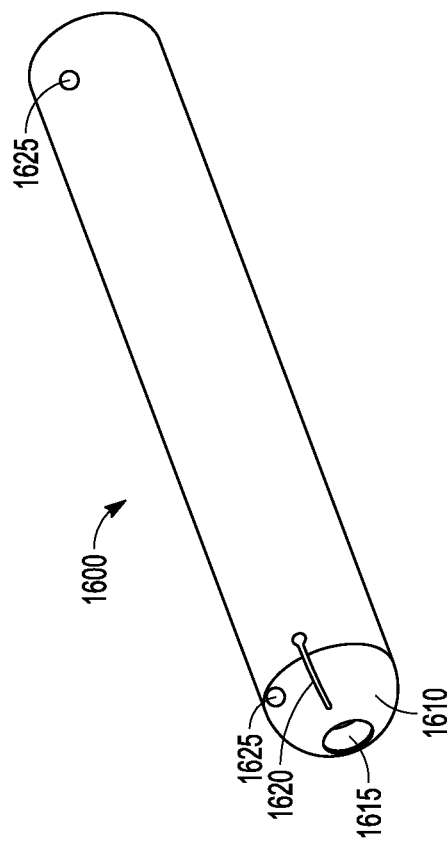
FIG. 16 is a line drawing representation of a sleeve having a reduced diameter tip according to an example embodiment.

FIG. 16 is a line drawing representation of a sleeve 1600 having a reduced diameter or compressed tip 1610. The tip 1610 has a hole 1615 in one embodiment, and a feature 1620 prior to tearing. The feature 1620 may comprise a slot or series of small holes or serrations in various embodiments to facilitate tearing to open the hole 1615 wider as previously shown. The tip may also include a mesh comprising a series of small holes designed to engage with the stent as the stent is being pushed out of the microcatheter. One or more markers 1625 may be positioned on each end of the sleeve 1600 to enable correct placement of the sleeve and stent during installation.

Figure 17:
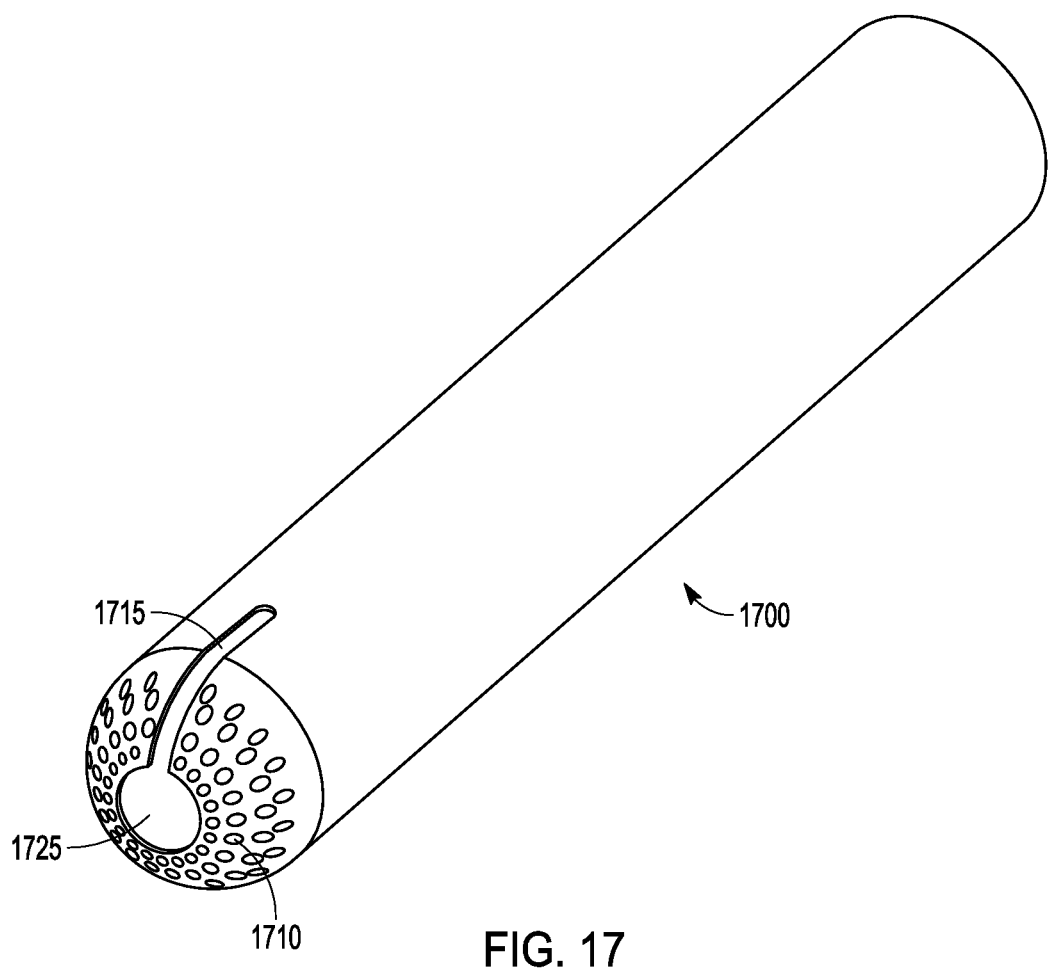
FIG. 17 is a line drawing of a sleeve that includes a meshed end according to an example embodiment.

FIG. 17 is a line drawing of a sleeve 1700 that includes a meshed end 1710 that is designed to catch a compressed stent end as it is being pushed out. Struts may be used to facilitate such catching, or the end of the stent itself may catch the meshed end. A feature 1715, such as a slot may also extend from an opening 1725 in the meshed end toward a main body of the sleeve. The slot may tear during installation of the sleeve on a stent to ensure fluid flow through a vessel is not impeded.

Figure 18:
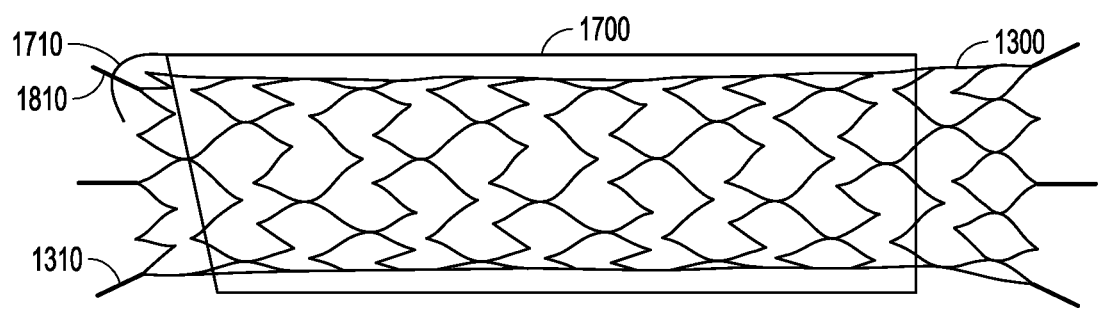
FIG. 18 is a side elevation representation of stent with a sleeve positioned around the stent according to an example embodiment.

FIG. 18 is a side elevation representation of stent 1300 with a sleeve 1700 positioned around the stent 1300. The representation is consistent with the stent having been pushed out of a microcatheter or held in position via a rod while the microcatheter is being withdrawn such that the sleeve 1700 is positioned as shown. Note that at least one strut 1310 has captured the meshed end 1710 of the sleeve as illustrated at 1810.

Figure 19:
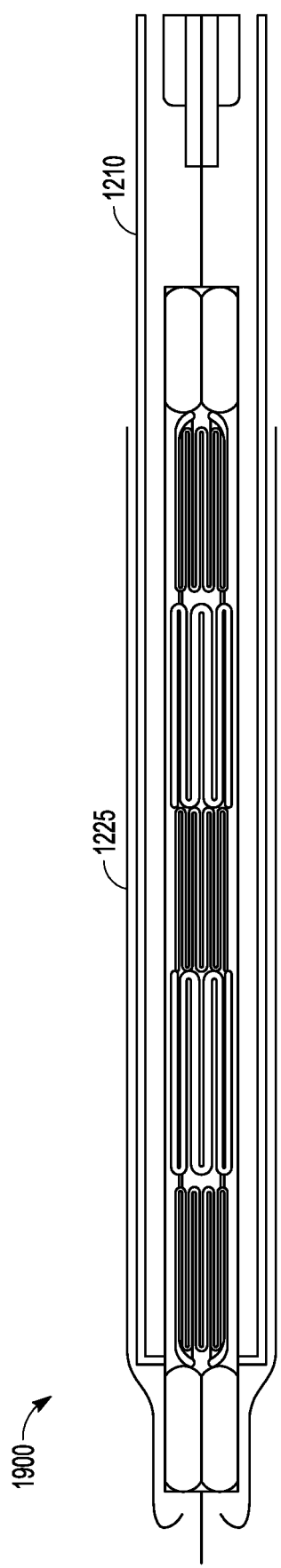
FIG. 19 is a cross section elevation representation of an alternative device for placing a sleeve coated stent according to an example embodiment.

FIG. 19 is a cross section elevation representation of an alternative device 1900. Reference numbers are the same in FIG. 19 as they are in FIG. 12. However, in FIG. 19, the sleeve 1225 is not protected by an outer sheath. Installation proceeds the same as previously described, with extrusion of the stent resulting in catching the sleeve and dragging the sleeve along an outer surface of the microcatheter.

EXAMPLES

1. A method includes placing a deformable sleeve-tipped catheter proximate an aneurysm in a blood vessel, positioning a stent through the catheter adjacent the aneurysm, and withdrawing the catheter such that the sleeve is captured by the stent and covers a portion of the stent to obstruct the aneurysm.

2. The method of example 1 wherein capturing the deformable sleeve comprises engaging a protrusion of the stent with a hole in the sleeve.

3. The method of any of examples 1-2 wherein the sleeve extends in a taper away from the tip of the catheter.

4. The method of any of examples 2-3 wherein the engaging protrusion comprises one or more struts and the hole comprises one or more holes, and where multiple of the struts are engaged with multiple of the holes.

5. The method of any of examples 1-4 and further comprising expanding the stent into retentive contact with the blood vessel about the aneurysm.

6. The method of any of examples 1-5 and further comprising expanding the stent and dilating the sleeve such that the sleeve becomes enmeshed in an outer surface of the stent.

7. The method of any of examples 1-6 wherein the sleeve comprises a polymer sleeve.

8. The method of example 7 wherein the polymer sleeve is coated with a drug.

9. The method of example 7 wherein the polymer sleeve is coated with cellular therapeutics.

10. The method of any of examples 1-9 wherein the catheter comprises a microcatheter and wherein the stent has a diameter less than 0.0762 mm.

11. The method of example 1 and further comprising detaching a cover portion of the sleeve to cover the stent from a tether portion of the sleeve attached to the catheter.

12. The method of example 11 wherein the tether portion of the sleeve comprises a plurality of perforations formed at a circumference of the sleeve at a predetermined axial location of the sleeve.

13. The method of any of examples 1-12 wherein the sleeve has an axial length of between 1 mm and 100 mm and the length.

14. The method of any of examples 1-13 wherein different portions of the sleeve are coated with different drugs.

15. The method of any of examples 1-14 wherein accessing the aneurysm comprises inserting the sleeve tipped catheter into an artery and moving the tip proximate the aneurysm.

16. The method of any of examples 1-16 wherein the captured sleeve operates to enhance the structural integrity of the stent.

17. A method including attaching a tether portion of a sleeve to a distal end of a catheter, placing the distal end of the catheter with the sleeve proximate to an aneurysm in a blood vessel, moving a stent through a lumen of the catheter, retentively engaging a first end of the stent with a distal end of the sleeve, and detaching the tether portion of the sleeve such that the sleeve covers at least a portion of the stent and blocks blood flow to the aneurysm.

18. A method including attaching a tether portion of a sleeve to a distal end of a catheter, placing the distal end of the catheter into a selected position within a vessel, moving a stent through a lumen of the catheter, retentively engaging a first end of the stent with a distal end of the sleeve, and detaching the sleeve about the tether portion such that the sleeve covers at least a portion of the stent at the selected position within the vessel.

19. The method of example 18 wherein retentively engaging a first end of the stent with a distal end of the sleeve comprises engaging a protrusion of the stent with a hole in the sleeve.

20. The method of any of examples 18-19 and further comprising expanding the stent and dilating the sleeve such that the sleeve becomes enmeshed in an outer surface of the stent.

21. A device including a catheter having a lumen and a distal end, a deformable sleeve having a proximal end coupled to the distal end of the catheter, the sleeve having a hole positioned at a distal end of the sleeve and adapted to engage a strut of a stent advanced through the catheter lumen, and the sleeve having an annular set of perforations positioned between the proximal end of the sleeve and the distal end of the sleeve.

22. The device of example 21 and further including a sheath disposed over at least a portion of the sleeve.

23. A deformable sleeve having a proximal end to couple to a distal end of a catheter, the sleeve including a hole positioned at a distal end of the sleeve and adapted to engage a strut of a stent advanced through a lumen of the catheter, and an annular set of perforations positioned between the proximal end of the sleeve and the distal end of the sleeve.

24. The sleeve of example 23 and further comprising a therapeutic coating on an outside of the sleeve.

25. The sleeve of example 24 wherein the therapeutic coating comprises a drug.

26. The sleeve of example 25 wherein the therapeutic coating comprises multiple drugs coating different portions of the outside of the sleeve.

27. The sleeve of example 25 wherein the therapeutic coating comprises cells.

28. The sleeve of example 27 wherein the sleeve comprises a polymer.

29. The sleeve of example 28 wherein the polymer comprises two or more polymers with different properties.

30. The sleeve of any of examples 23-29 wherein the polymer comprises a copolymer blend or layers of polymers.

31. The sleeve of any of examples 23-30 wherein the sleeve has a wall thickness of between 0.00635 mm and 0.127 mm.

32. The sleeve of any of examples 23-31 wherein the sleeve has a length between the perforations and distal end of between 1 mm-100 mm.

33. The sleeve of any of examples 23-32 wherein the sleeve is tapered from the proximal end to the distal end.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A method comprising:
    placing a catheter, having a first end of a deformable sleeve coupled to a tip of the catheter, proximate an aneurysm in a blood vessel;
    positioning a stent through the placed catheter adjacent the aneurysm; and
    withdrawing the catheter such that a second end of the deformable sleeve is captured by the stent and covers a portion of the stent to obstruct the aneurysm, wherein the deformable sleeve is captured by engaging a protrusion of the stent with a hole in the second end of the sleeve.

2. The method of claim 1 wherein the second end of the sleeve extends in a taper away from the tip of the catheter.

3. The method of claim 1 wherein the engaging protrusion comprises one or more struts and the hole comprises one or more holes, and where multiple of the struts are engaged with multiple of the holes.

4. The method of claim 1 and further comprising expanding the stent into retentive contact with the blood vessel about the aneurism.

5. The method of claim 1 and further comprising expanding the stent and dilating the sleeve such that the sleeve becomes enmeshed in an outer surface of the stent.

6. The method of claim 1 wherein the sleeve comprises a polymer sleeve.

7. The method of claim 6 wherein the polymer sleeve is coated with a drug.

8. The method of claim 6 wherein the polymer sleeve is coated with cellular therapeutics.

9. The method of claim 1 wherein the catheter comprises a microcatheter and wherein the stent has a diameter less than 0.762 mm.

10. The method of claim 1 and further comprising detaching a cover portion of the sleeve to cover the stent from the first end of the sleeve comprising a tether portion of the sleeve attached to the catheter.

11. The method of claim 10 wherein the tether portion of the sleeve comprises a plurality of perforations formed at a circumference of the sleeve at a predetermined axial location of the sleeve.

12. The method of claim 1 wherein the sleeve has an axial length of between 1 mm and 100 mm.

13. The method of claim 1 wherein different portions of the sleeve are coated with different drugs.

14. The method of claim 1 wherein accessing the aneurysm comprises inserting the catheter and sleeve into an artery and moving the tip of the catheter proximate the aneurysm.

15. The method of claim 1 wherein the captured sleeve operates to enhance the structural integrity of the stent.

16. A method comprising:
    attaching a tether portion of a sleeve to a distal end of a catheter;
    placing the distal end of the catheter into a selected position within a vessel;
    moving a stent through a lumen of the placed catheter;
    retentively engaging a first end of the stent with a distal end of the sleeve; and
    detaching the sleeve about the tether portion such that the sleeve covers at least a portion of the stent at the selected position within the vessel, wherein retentively engaging the first end of the stent with a distal end of the sleeve comprises engaging a protrusion of the stent with a hole in the sleeve.

17. The method of claim 16 and further comprising expanding the stent and dilating the sleeve such that the sleeve becomes enmeshed in an outer surface of the stent.

* * * * *